(12) United States Patent  (10) Patent No.: US 8,486,644 B2
Bouzid et al.  (45) Date of Patent: Jul. 16, 2013

(54) CHEMILUMINESCENCE COMPACT IMAGING SCANNER

(75) Inventors: Ahmed Bouzid, Lincoln, NE (US); Chris Lesiak, Lincoln, NE (US); Daniel W. Konz, Lincoln, NE (US); David L. Franzen, Lincoln, NE (US); William Biggs, Lincoln, NE (US); Jon P. Anderson, Lincoln, NE (US)

(73) Assignee: Li-Cor, Inc., Lincoln, NE (US)

( * ) Notice: Subject to any disclaimer, the term of this patent is extended or adjusted under 35 U.S.C. 154(b) by 0 days.

(21) Appl. No.: 13/432,410

(22) Filed: Mar. 28, 2012

(65) Prior Publication Data

US 2013/0157282 A1  Jun. 20, 2013

Related U.S. Application Data

(60) Provisional application No. 61/576,941, filed on Dec. 16, 2011.

(51) Int. Cl.
*G01N 33/53* (2006.01)

(52) U.S. Cl.
USPC .......................................................... 435/7.1

(58) Field of Classification Search
None
See application file for complete search history.

(56) References Cited

U.S. PATENT DOCUMENTS

| | | | | |
|---|---|---|---|---|
| 4,200,892 A * | 4/1980 | Weimer | ......................... | 348/310 |
| 4,208,094 A * | 6/1980 | Tomlinson et al. | .............. | 385/18 |
| 4,382,672 A * | 5/1983 | Boykin | ............................... | 355/1 |
| 4,819,070 A * | 4/1989 | Hynecek | ........................ | 348/302 |
| 4,845,552 A * | 7/1989 | Jaggi et al. | ..................... | 382/128 |
| 4,922,335 A * | 5/1990 | Outa et al. | ..................... | 358/506 |
| 5,053,887 A * | 10/1991 | Thompson | ..................... | 358/3.2 |
| 5,069,769 A | 12/1991 | Fujimiya et al. | | |
| 5,299,272 A * | 3/1994 | Buchin | ............................ | 385/34 |
| 5,459,325 A | 10/1995 | Hueton et al. | | |
| 5,504,527 A | 4/1996 | Philbrick et al. | | |
| 5,528,050 A | 6/1996 | Miller et al. | | |
| 5,537,075 A * | 7/1996 | Miyazaki | ........................ | 327/566 |
| 5,953,133 A * | 9/1999 | Fujimiya et al. | ............... | 358/474 |

(Continued)

FOREIGN PATENT DOCUMENTS

| | | |
|---|---|---|
| EP | 1 985 995 A2 | 10/2008 |
| JP | 3012794 A | 8/1997 |
| WO | 99/53288 A2 | 10/1999 |

OTHER PUBLICATIONS

Baltsavias (1998) ISPRS Commission I Symposium, Bangalore, India, in IAPRS, vol. 32, Part 1, p. 1-9.*

(Continued)

*Primary Examiner* — Nelson C. Yang
*Assistant Examiner* — Richard Moerschell
(74) *Attorney, Agent, or Firm* — Kilpatrick Townsend & Stockton LLP

(57) ABSTRACT

Systems, devices, and methods for accurately imaging chemiluminescence and other luminescence are disclosed. A compact, flat-bed scanner having a light-tight enclosure, one or more detector bars of linear charge-coupled device (CCD) or complementary metal oxide semiconductor (CMOS) imaging chips, and high working numerical aperture (NA) optics scans closely over a sample in one direction and then the opposite direction. Averages or other combinations of intensity readings for each pixel location (x, y) between the two or more passes are averaged together in order to compensate for luminescence that varies over time. On-chip pixel binning and multiple clock frequencies can be used to maximize the signal to noise ratio in a CCD-based scanner.

19 Claims, 9 Drawing Sheets

U.S. PATENT DOCUMENTS

| | | | |
|---|---|---|---|
| 5,991,030 | A | 11/1999 | Yamamoto et al. |
| 6,072,570 | A * | 6/2000 | Chipman et al. ............. 356/124 |
| 6,172,785 | B1 | 1/2001 | Wulf |
| 6,320,196 | B1 | 11/2001 | Dorsel et al. |
| 6,373,074 | B1 | 4/2002 | Mueller et al. |
| 6,492,655 | B2 | 12/2002 | Yasuda |
| 6,495,849 | B2 | 12/2002 | Yasuda |
| 6,529,239 | B1 * | 3/2003 | Dyck et al. .................... 348/279 |
| 6,867,851 | B2 | 3/2005 | Blumenfeld et al. |
| 7,163,822 | B2 | 1/2007 | Yazawa et al. |
| 7,345,796 | B2 | 3/2008 | Sasama |
| 7,537,934 | B2 | 5/2009 | Sundararajan et al. |
| 7,649,618 | B2 | 1/2010 | Tuschel et al. |
| 7,727,471 | B2 | 6/2010 | Hsieh et al. |
| 7,773,223 | B2 | 8/2010 | Ikami |
| 2002/0054715 | A1 * | 5/2002 | Os et al. ....................... 382/276 |
| 2003/0193597 | A1 * | 10/2003 | Fossum et al. ............... 348/308 |
| 2003/0197127 | A1 * | 10/2003 | Wainer et al. ............ 250/363.02 |
| 2004/0041939 | A1 * | 3/2004 | Hofer et al. .................... 348/362 |
| 2004/0051808 | A1 | 3/2004 | Akhavan-Tafti et al. |
| 2004/0224332 | A1 * | 11/2004 | Loney ............................... 435/6 |
| 2005/0105097 | A1 * | 5/2005 | Fang-Yen et al. ............ 356/497 |
| 2006/0072179 | A1 * | 4/2006 | Caster et al. .................. 359/202 |
| 2007/0080305 | A1 | 4/2007 | Maitrejean et al. |
| 2007/0176079 | A1 * | 8/2007 | Wany ......................... 250/208.1 |
| 2007/0194121 | A1 | 8/2007 | Yang et al. |
| 2007/0259389 | A1 * | 11/2007 | Mastroianni et al. ............. 435/8 |
| 2008/0240747 | A1 | 10/2008 | Ikami |
| 2009/0141132 | A1 | 6/2009 | Lehmann et al. |
| 2010/0178667 | A1 * | 7/2010 | Benjamin .................... 435/40.5 |
| 2010/0248387 | A1 | 9/2010 | Gambini et al. |
| 2011/0192990 | A1 | 8/2011 | Hennecke |
| 2011/0279706 | A1 | 11/2011 | Lesiak et al. |
| 2011/0286993 | A1 * | 11/2011 | Jensen et al. ................. 424/94.6 |
| 2012/0142086 | A1 | 6/2012 | Haguet et al. |

OTHER PUBLICATIONS

Abnova, Photon™—96 well Chemiluminescence System user manual, www.abnova.com, 22 pages.

"Aperio Introduces New Fluorescence Scanner for Whole Slide Imaging of Immunofluorescence and Analysis of Biomarker Expression," http://www.medicalnewstoday.com/releases/146908.php, Article date Apr. 22, 2009, print date Jan. 16, 2012, 4 pages.

Carestream, Gel Logic 6000 Pro, http://www.carestream.com/publiccontent.aspx?langtype=1033&id=452325, print date Jan. 16, 2012, 1 page.

Dewey et al., "A charge-coupled-device camera image analysis system for quantifying DNA distributions in agarose gels after pulsed-field gel electrophoresis," Radiat Res., 1994, vol. 140(1), pp. 37-47.

GE Healthcare Life Sciences, ImageQuant™ LAS 4000 Biomolecular Imager, http://www.gelifescienses.com/aptrix/upp01077.nsf/content/products?opendocuments&pa . . . , print date Jan. 16, 2012, 2 pages.

Leica SCN400 F, Brightfield and Fluorescence Slide Scanner Leica SCN400 F, http://www.lecia-microsystems.com/products;digital-pathology/scan/details/products/leica-s . . . , print date Jan. 16, 2012, 2 pages.

MiraiBio, Imaging Product Line, FMBIO brochure, 6 pages.

Miura "Imaging and detection technologies for image analysis in electrophoresis," Electrophoresis, 2001, vol. 22, pp. 801-813.

Porakishvili, et al., "A low budget luminometer for sensitive chemiluminescent immunoassays," Journal of Immunological Methods, vol. 234(1-2), 2000, pp. 35-42.

Syngene, ProteomeScan, Scanner Imaging System brochure, *pages.

UVP, BioSpectrum® Imaging System, http://www.uvp.com/biospectrum.html, print date Jan. 16, 2012, 3 pages.

UVP, ChemiDoc-It®$^{TS2}$ Imager, http://www.uvp.com/chemidocitTS2.html, print date Jan. 16, 2012, 3 pages.

Weisfield et al., "Electronic noise analysis of a 127-micron pixel . . . ," Proceedings of SPIE, 2001, vol. 4320, pp. 209-218.

Xu et al., "Study on the chemiluminescence resonance energy transfer between luminol and fluorescent dyes using a linear CCD spectrometer," Journal of Luminescence, vol. 130(10), 2010, pp. 1872-1879.

Baltsavias, "Photogrammetric scanners-survey, technological developments and requirements," IAPRS, 1998, vol. 32(1), pp. 1-9.

Mircotek Scan the World, Bio-5000 brochure, http://www.microtek.com, 2 pages.

Annex to Form PCT/ISA/206, Communication Relating to the Results of the Partial International Search, PCT application No. PCT/US2012/030979, 3 pages.

Abnova's System Products, Photon™—96 well Chemiluminescence Reader, http://www.abnova.com/new_products/system/photon_96_well_chemiluminescence_Read . . . , printed date Jan. 16, 2012, 4 pages.

Aperio, ScanScope FL System-Multichannel Fluorescence Whole-Slide Scanning, http://www.aperio.com/pathdogy-services/scanscope-FL-system-slides.asp, print date Jan. 16, 2012, 1 page.

Boniszewski et al., "The use of charge-coupled devices in the quantitative evaluation of images, on photographic film or membranes, obtained following electrophoretic separation of DNA fragments," Electrophoresis, 1990, vol. 11(5), pp. 432-440.

"Capture the Perfect Image for Winning Results," Jan. 1, 2008, http://home.thgeyer.de/fileadmin/user_assets/documents/GE_Healthcare/Capture_the_perfect_image.pdf, retrieved on Jun. 22, 2012.

Hooper et al., "Quantitative luminescence imaging in the biosciences using the CCD camera: Analysis of macro and micro samples," TrAC Trends in Analytical Chemistr1990, vol. 9(8), pp. 269-277.

Karger et al., "Line scanning system for direct digital chemiluminescence imaging of DNA sequencing blots," Anal Chem., 1993, vol. 65(13), pp. 1785-1793.

Li-Cor, Odyssey® CLx, Infrared Imaging System, http://www.licor.com/bio.products/imaging_systems/odyssey/odsssey_imager.jsp, print date Jan. 16, 2012, 1 page.

Maxwell Sensors Inc., FS-Scanner TM, http//:www.maxwellsensors.com/fs-scanner.htm, print date Jan. 16, 2012, 2 pages.

MiraiBio, FMBIO Overview, http://www.miraibio.com/fmbio/fmbio-overview.html, print date Jan. 16, 2012, 3 pages.

Mircotek, Bio-5000, http://www.microtek.com.tw/products.php?kindID=5&ID=18, print date Jan. 16, 2012, 4 pages.

Syngene, 2D/1D gel image scanner-ProteomeScan, http://www.syngene.com/proteomescan/, print date Jan. 16, 2012, 1 page.

International Search Report and Written Opinion, Sep. 25, 2012, PCT application No. PCT/US2012/030979, 18 pages.

* cited by examiner

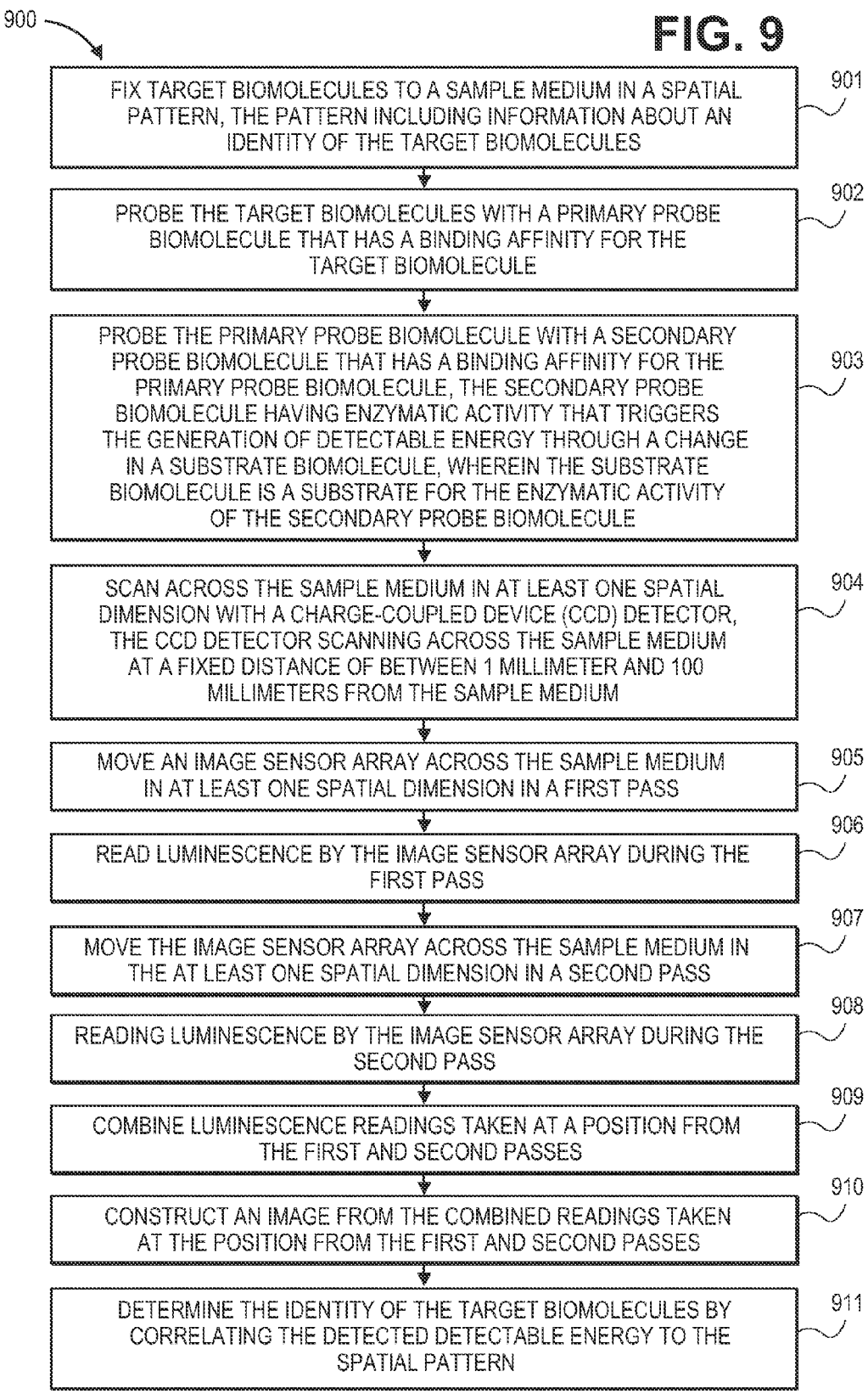

CHEMILUMINESCENCE COMPACT IMAGING SCANNER

CROSS-REFERENCES TO RELATED APPLICATIONS

This application claims the benefit of U.S. Provisional Patent Application No. 61/576,941, filed Dec. 16, 2011, the contents of which are hereby incorporated by reference in its entirety for all purposes.

STATEMENT AS TO RIGHTS TO INVENTIONS MADE UNDER FEDERALLY SPONSORED RESEARCH OR DEVELOPMENT

Not Applicable

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND

1. Field of the Invention

Generally, this application relates to molecular biology and microbiology chemistry processes and apparatuses including optical measuring or testing means. Certain embodiments relate to devices, systems, and methods for imaging assays exhibiting chemiluminescence or other luminescence.

2. Background

Detecting and identifying certain biomolecules can be important in studying biological systems, such as plants and animals. Such systems may exhibit only small amounts of a biomolecule, such as a protein, which in some instances may only be accurately measured by high-end, laboratory-grade equipment and processes. Many assay techniques have been developed over the last decades for accurately acquiring such measurements.

A variety of assays use enhanced chemiluminescence (CL) to detect small quantities of a biomolecule. Techniques using an Enzyme-linked Immunosorbent Assay (ELISA) or a Western Blot are often used to detect low abundance proteins.

Chemiluminescence techniques differ from fluorescence in that no outside excitation light is needed. Therefore, there is virtually no light emission from areas of the assay where the chemiluminescence reaction is not happening, and thus there exists a very low optical background. This is one of the primary reasons for the ability to detect low amounts of optical emissions in CL assays.

Chemiluminescence emitted optical signals are typically characterized by: being 1) weak and 2) non-constant over time. Weakness of the optical signals drives the need for high signal-to-noise detection methods. The use of high-efficiency imaging optics and extremely low noise detectors are taught in the art for measuring chemiluminescence. The non-constant nature of light emission of typical chemiluminescence substrates naturally implies using whole-image capturing methods. Such imaging allow for collecting equal amounts of light from all emitting areas of the assay at the same time and over long integration times.

In the past, one of the most common methods for capturing optical emissions from a CL assay was the use of photographic film. One would expose a photographic film in close proximity to a light-emitting Western Blot, for example. However, there are a number of limitations to using film. Oftentimes, film exhibits a non-linear response to impinging photons and has limited dynamic range. There is also the need for careful handling of undeveloped film and special darkroom facilities and chemicals to develop and process the film.

Furthermore, there is often a need to digitally capture an image of the assay in order to store it for future reference. To accomplish this, film users often capture an image of developed film using a digital camera or a flat-bed scanner. This approach requires additional imaging equipment, can be non-quantitative, and is prone to errors in image capture and reproduction.

Directly imaging the optical emissions of a CL assay using a digital, Charge-Coupled Device (CCD) camera can overcome many of the difficulties associated with using photographic film. CCD cameras provide a linear response to impinging photons over a wide dynamic range, no chemicals are needed for developing, and digital data can be read directly from the digital camera and easily stored for further analysis and quantification. Exposing a high-quality, cryogenically-cooled CCD array to a Western Blot over a long period of time in a very dark room has been taught in the art. A number of such CCD-based imagers exist on the market nowadays that achieve sensitivity that is comparable to film. An example of a CCD-based imager is the LI-COR Odyssey® Fc imager. The CCD-based imagers have deeply cooled chips that are highly sensitive to light.

Complementary Metal Oxide Semiconductor (CMOS) image sensors have been developed in parallel with CCD sensors. Unlike those for CCDs, each pixel in a CMOS image sensor has its own charge-to-voltage conversion components. This can result in lower uniformity than CCD image sensors. However, as lithographic and other manufacturing processes improve, CMOS image sensor uniformity has become less of an issue. As the technology improves, CMOS image sensor arrays may be used in place of CCD image sensor arrays in many markets.

There exists a need in the art for a small, inexpensive, digital alternative to CL imaging by film that attains the same or better sensitivity.

BRIEF SUMMARY

The present application is related to a compact, flat-bed scanner for capturing images of very dim chemiluminescence or other luminescence from an assay without the need for deeply cooled CCDs. Under a light-tight cover in an embodiment, a detector bar of linear CCDs and high working numerical aperture (NA) optics is swept in close proximity to a sample exhibiting chemiluminescence in order to capture light. The detector bar is then swept back in the opposite direction to capture more light. Because of the extremely low light from chemiluminescence and commensurate dearth of photons for the CCD to pick up, each sweep or pass might take a few minutes. A final image is constructed by taking an average of—or otherwise combining—the two (or more) pixel readings at each point from the first and second passes so as to compensate for changing luminescence over the few minutes that it takes for the scans. More passes can be used as well.

The detector bar can have staggered columns of low-cost, uncooled linear CCD integrated circuits (ICs). Multiple detector bars can be used to sweep across the sample, which can shorten the scan time, minimizing the effect of the sample's changing luminescence over time. On-chip binning can combine multiple pixel readings together before they are read off a CCD chip, and novel clocking mechanisms can facilitate clean data collection. In some embodiments, the detector bar moves and the sample stays still, while in other embodiments the opposite occurs.

Some embodiments of the present invention are related to a luminescence scanner apparatus. The apparatus includes a sample bed configured to hold a luminescent sample medium, a detector bar comprising one or more image sensor arrays, each sensor array having a plurality of pixel elements, the pixel elements of each sensor array adapted to detect photons simultaneously with one another, the detector bar configured to move with respect to the sample bed, a motor configured to move the detector bar with respect to the sample bed in a first pass in a first direction and then move the detector bar with respect to the sample bed in a second pass in a second direction opposite the first direction, a circuit adapted to combine a pixel reading from a position in the first pass with a pixel reading from the position in the second pass, and a circuit adapted to construct a two-dimensional image from the combined pixel readings.

The embodiments can combine the pixel readings by averaging pixel readings at each location from the first and second (or more) passes. The one or more image sensor arrays can include linear CCD integrated circuits (ICs) staggered with respect to each other along the detector bar and so that they overlap longitudinally.

The embodiments can include a second detector bar comprising one or more image sensor arrays, the second detector bar configured to move with respect to the sample bed, wherein the detector bars are configured to predominantly scan over different, non-overlapping areas of the sample bed, and a circuit configured to construct the two-dimensional image from pixel readings from both the detector bars. Minimal overlap may be employed to facilitate image registration and reconstruction.

A gradient index (GRIN) lens array can be disposed between the sample bed and the one or more linear image sensor arrays, the GRIN lens array having a working numerical aperture (NA) of greater-than-or-equal-to 0.10, 0.20, 0.25, or more. The GRIN lens array can be disposed between 1 and 100 millimeters of a sample positioned by the sample bed.

Some embodiments are directed to a luminescence scanner apparatus. The apparatus includes a sample bed configured to hold a luminescent sample medium, an integrated circuit (IC) charge-coupled device (CCD) image sensor array having a plurality of pixel elements, the pixel elements adapted to store photon-induced charges simultaneously with one another, the image sensor array configured to move with respect to the sample bed, a motor configured to move the image sensor array with respect to the sample bed, a circuit adapted to sum multiple photo-charges from adjacent CCD pixel elements into a readout capacitor of the CCD image sensor array, and a circuit adapted to read the summed photo-charges from the readout capacitor and construct an image using the summed photo-charges.

The method apparatus can further include a circuit adapted to apply two or more distinct CCD clock frequencies to an input of each of the one or more integrated circuit CCD image sensor arrays, the input adapted to shift photon-induced charges from the pixel elements to an output of the integrated circuit CCD image sensor array.

Some embodiments are directed to a luminescence scanner apparatus. The apparatus includes a sample bed configured to hold a luminescent sample medium, an integrated circuit (IC) charge-coupled device (CCD) image sensor array having a plurality of pixel elements, the pixel elements adapted to store photon-induced charges simultaneously with one another, the image sensor array configured to move with respect to the sample bed, a motor configured to move the image sensor array with respect to the sample bed, a circuit adapted to apply two or more distinct CCD clock frequencies to an input, such as a pin, of the integrated circuit CCD image sensor array, the input adapted to shift photon-induced charges from the pixel elements to an output of the integrated circuit CCD image sensor array, and a circuit adapted construct an image from the output of the integrated circuit CCD image sensor array.

Some embodiments are directed to a method for acquiring an image of a luminescent medium. The method includes placing a luminescent medium within an enclosure of a scanning device, moving an image sensor array in a first direction with respect to the luminescent medium in a first pass across the luminescent medium, the image sensor array having a plurality of pixel elements adapted to detect photons simultaneously with one another, detecting luminescence using the pixel elements during the first pass, moving the image sensor array in a second direction with respect to the luminescent medium in a second pass across the luminescent medium, the second direction being opposite the first direction, combining a pixel reading from a position in the first pass with a pixel reading from the position in the second pass, and constructing an image from the combined pixel readings from the first and second passes Some embodiments are directed to a method for acquiring an image from a luminescent medium. The method can include fixing target biomolecules to a sample medium in a spatial pattern, the pattern including information about an identity of the target biomolecules, probing the target biomolecules with a primary probe biomolecule that has a binding affinity for the target biomolecule, and probing the primary probe biomolecule with a secondary probe biomolecule that has a binding affinity for the primary probe biomolecule, the secondary probe biomolecule having enzymatic activity that triggers the generation of detectable energy through a change in a substrate biomolecule, whereby the substrate biomolecule is a substrate for the enzymatic activity of the secondary probe biomolecule. The method further includes moving an image sensor array across the sample medium in at least one spatial dimension in a first pass, reading luminescence by the image sensor array during the first pass, and constructing an image from the luminescence read by the image sensor array.

The method can further include moving the image sensor array across the sample medium in the at least one spatial dimension in a second pass, reading luminescence by the image sensor array during the second pass, combining luminescence readings taken at a position from the first and second passes, and constructing the image from the combined readings taken at the position from the first and second passes.

The embodiments can use various sample mediums, including membranes (e.g., nylon or nitrocellulose), plates, glass or plastic surfaces, etc.

With reference to the remaining portions of the specification, including the drawings and claims, one of ordinary skill in the art will realize other features and advantages of the present invention. Further features and advantages of the present invention, as well as the structure and operation of various embodiments of the present invention, are described in detail below with respect to the accompanying drawings. In the drawings, like reference numbers indicate identical or functionally similar elements.

BRIEF DESCRIPTION OF THE DRAWINGS

FIG. 9 is a flowchart of a process in accordance with an embodiment.

DETAILED DESCRIPTION

Figure 1A:
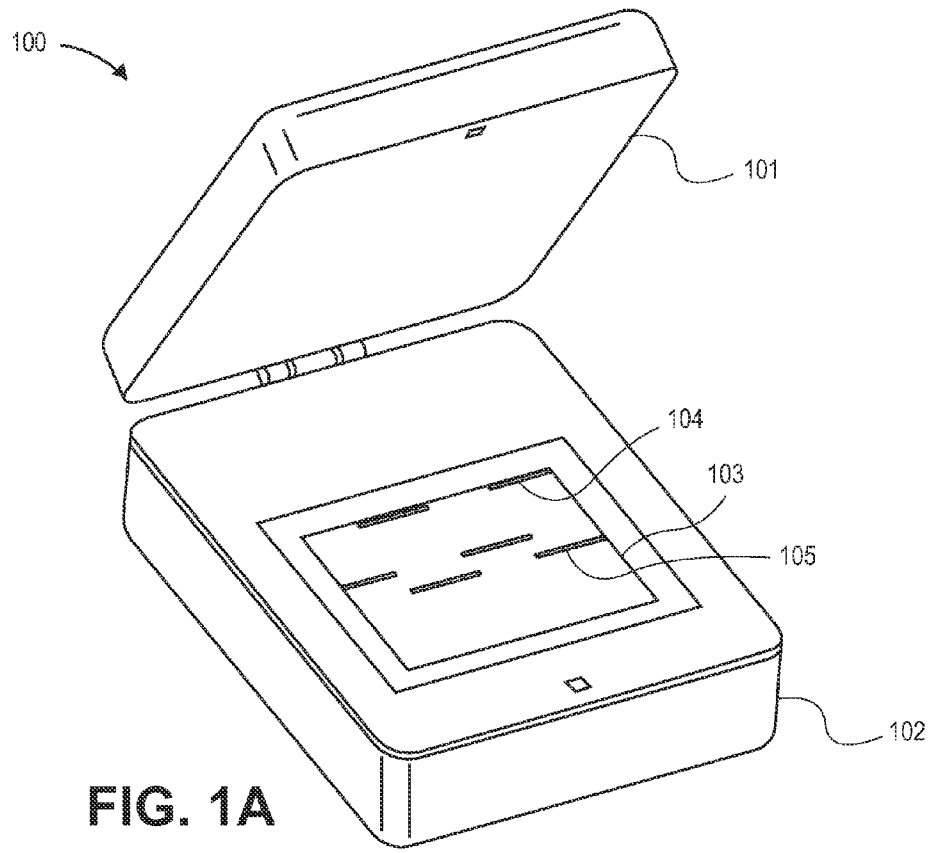
FIG. 1A illustrates a compact imaging scanner in accordance with an embodiment.

Presented herein is a novel imaging method and apparatus that achieves the sensitivity of high-end CCD imagers but with a significantly smaller size and without the need for cooling. The imaging apparatus can therefore be produced and maintained at a much lower cost than before.

In chemiluminescence imagers of the prior art, the choice of the CCD, its packaging, and its electronics are often primarily driven by the need for low total noise. This typically requires the use of high-end, scientific CCDs. These scientific CCDs are typically small in size, in the range of 1 centimeter (cm)×1 cm. The size of a typical Western Blot is on the order of 10 cm×10 cm. Thus, low NA lenses and other imaging optics are needed to project the sample area onto to the smaller CCD area at the appropriate focal lengths. Such imaging requires a total optical path of hundreds of millimeters (mm), which results in a physically large imager.

The larger the sample, the longer the working distance. The longer the working distance, the lower the collection efficiency of the lenses. This causes the need to collect light for a longer periods of time, and this in turn invariably requires even low-noise, scientific CCDs to be cooled in order to keep internal dark (thermal) noise under control. These conditions are among the reasons for the relatively high cost of CCD-based chemiluminescence imagers of the prior art.

Terms

A "Limit-of-Detection (LOD)" includes a smallest concentration of a sample that can be reliably detected, producing a signal that is three times as large as the standard deviation of the system noise level, or as otherwise known in the art.

An "image sensor array" includes sensors of CCD, CMOS, and other technologies that can detect light or other electromagnetic radiation contemporaneously in multiple pixels, its pixels arranged in a one-dimensional, two-dimensional, or other array, and as otherwise known in the art. An image sensor array with pixels arranged in one-dimension (i.e., a line) can include a linear CCD or a linear CMOS sensor, for example.

A "linear CCD" includes a charge-coupled device that is substantially longer and has more elements in one direction than another, orthogonal direction or as otherwise known in the art. An example of a widely available linear CCD is a Toshiba CCD Linear Image Sensor model TCD1205DG. It has 2,048 pixels, each pixel being 14 μm long (along the longitudinal length of the array, y-axis) and 200 μm wide (along the lateral width of the array, x-axis).

"Luminescence" includes an emission of light that is not due to incandescence or as otherwise known in the art. Luminescence includes chemiluminescence, bioluminescence, electroluminescence, phosphorescence, and other emissions that do not require optical illumination during imaging. Chemiluminescence is due to a chemical reaction and is one of the most common types of luminescence used to detect low abundance proteins. Bioluminescence is stimulated naturally by a living organism. Electroluminescence is electrically induced light emission. Phosphorescence is induced by optical charge prior to light emission.

A "luminescent sample medium" includes a medium adapted to support or contain a luminescent sample or as otherwise known in the art. Such mediums include membranes, such as nylon membranes or nitrocellulose membranes, which are typically used for Western Blot assays. Such mediums can include wells, such as MICROTITER® microwell plates and micro plates or other well plates of different shapes and sizes, which are typically used for ELISA assays. Such mediums can also include flat surfaces such as glass, plastic, etc.

"Deep cooling" includes active cooling below 10 degrees Celsius (° C.), 0° C., or other low temperatures including cryogenic and non-cryogenic temperatures.

"Binning" of pixels includes combining two or pixels into one effectively larger pixel. For example, three 14 μm-long pixels can be combined to create one effective pixel that is approximately 3×14 μm=42 μm long. The larger the pixel, the more light it collects. Larger pixels typically require more cooling for long (e.g., greater than 100 second) exposures. "On-chip binning" is described below.

A "gradient-index (GRIN) lens" includes a lens that has a variable refractive index. An example of a GRIN lens is Nippon Sheet Glass Ltd. Co. (NSG Group) SELFOC® microlens array model SLA-20BG-138-570-2R, distributed in the U.S. by Go!Foton Corp. of Somerset, N.J. SELFOC® microlenses are imaging lens rods. They are typically much shorter in length and larger in diameter than light delivery fibers (e.g., fiber optic cables). They often have properties that fiber guides do not have, such as radially varying indexes of refraction. The model SLA-20BG microlens has a high NA that helps with light collection, and it is short in length. It has two rows of 1:+1 imaging GRIN-rod lenses that are 6.89 mm-long, a working distance of 3.46 mm, and an effective line imaging NA of approximately 0.5 at a light wavelength of 570 nanometers (nm). The diameter of each SLA lenses is approximately 1 mm.

A "sample bed" includes an area for accommodating a sample and as otherwise known in the art. Examples of a sample bed include the area immediately above a glass or plastic plate that supports a sample while it is being scanned, the space that a microwell plate or micro plate is configured to be slid into by tray slots or drawer bearings, or other sample areas as known in the art.

Technical Advantages

There are several technical advantages of embodiments of the present invention over the prior art. Scanning closely over a sample, instead of imaging the entire sample at once through lenses, allows more light to be collected from dim luminescence. High NA optics and large effective pixel sizes can be used to maximize the amount of photons collected. For imaging a plate with wells that have some depth to them, scanning closely over the sample provides an additional benefit in comparison to wide area imagers. Area imagers are known to have a distortion artifact, known as parallax, which results from the fact that the imaging optics looks at the wells from different angles. Scanning closely avoids the parallax problem and produces images of all wells in the same manner with minimal distortion.

Even when scanning very closely over a sample with an almost perfect photoreceptor in a CCD, there are still too few photons from typical chemiluminescence to scan quickly. It can take minutes to scan 10 cm and collect sufficient light. In this time, however, the intensity of chemiluminescence changes. A different baseline of photons would be collected between the beginning and end of the scan, and a resulting image would be incorrectly dimmer at one end than the other. For at least this reason, scanning over time would not be an obvious choice for imaging chemiluminescence. Nevertheless, the inventors have determined that a two pass scan (i.e., scanning in one direction and then scanning in the other direction) and then averaging or otherwise combining points from the scans can sufficiently compensate for the variability of typical chemiluminescence.

Regarding cooling of a CCD, what often complicates the design for a low light CCD sensor is deep cooling. Deep cooling for CCDs can be at temperatures well below 0° C. In order to achieve that kind of temperature without condensation, the CCD should be packaged with a sealing mechanism. The sealing mechanism can drive up the cost and size of the camera as well as add maintenance and ruggedness issues. For cameras or wide area imagers that need to collect light for greater than 100 seconds, virtually any CCD, astronomic, scientific, or otherwise, needs to be cooled to well below 0° C. in order to keep its noise levels within reason. However, the inventors have found that an uncooled CCD or CCD that is not deeply cooled can be used in a practical, room temperature embodiment, keeping costs down and maintenance simple.

Figures

Figure 1B:
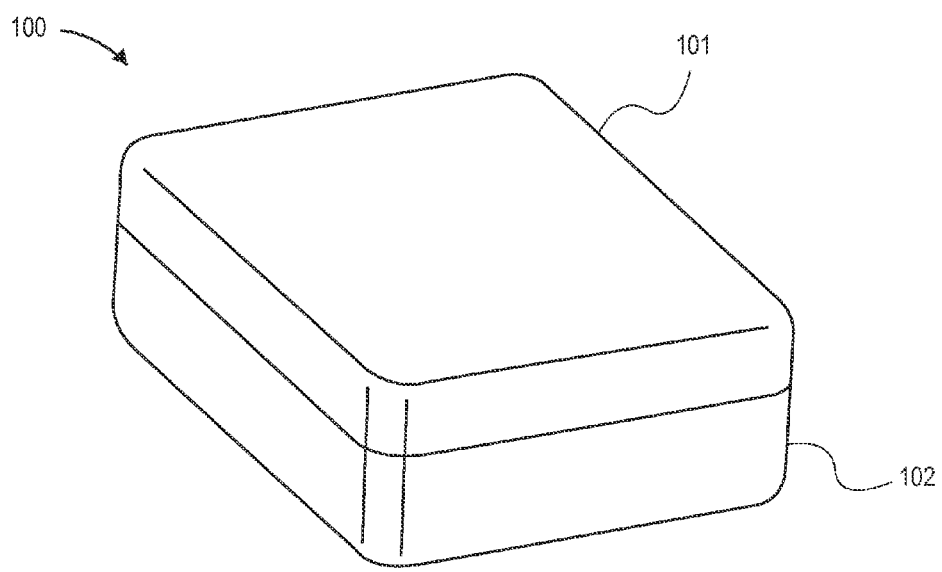
FIG. 1B illustrates the scanner of FIG. 1A with its lid closed.

FIGS. 1A-1B illustrate a compact imaging scanner in accordance with an embodiment. Luminescence scanner apparatus 100 is shaped like a flat-bed, paper document-style scanner and includes lid 101, base 102, and sample bed 103. Sample bed 103 includes transparent glass or plastic as a support and is able to hold wet membranes. Two imaging scanning bars, detector bar 104 and detector bar 105, are available for scanning Detector bar 104 is parked off the upper side of the sample area while detector bar 105 is parked in the center of the sample area.

A tray system can be implemented in which a technician can slide or carefully drop a tray into place over the scanning area. To minimize the distance and amount of glass or plastic between the sensitive scan bars and the luminescent material, the plates can be supported by bearing surfaces on the sides with no glass underneath. A well plate can be suspended at just the right focal/working distance over the detector bar(s).

Figure 2:
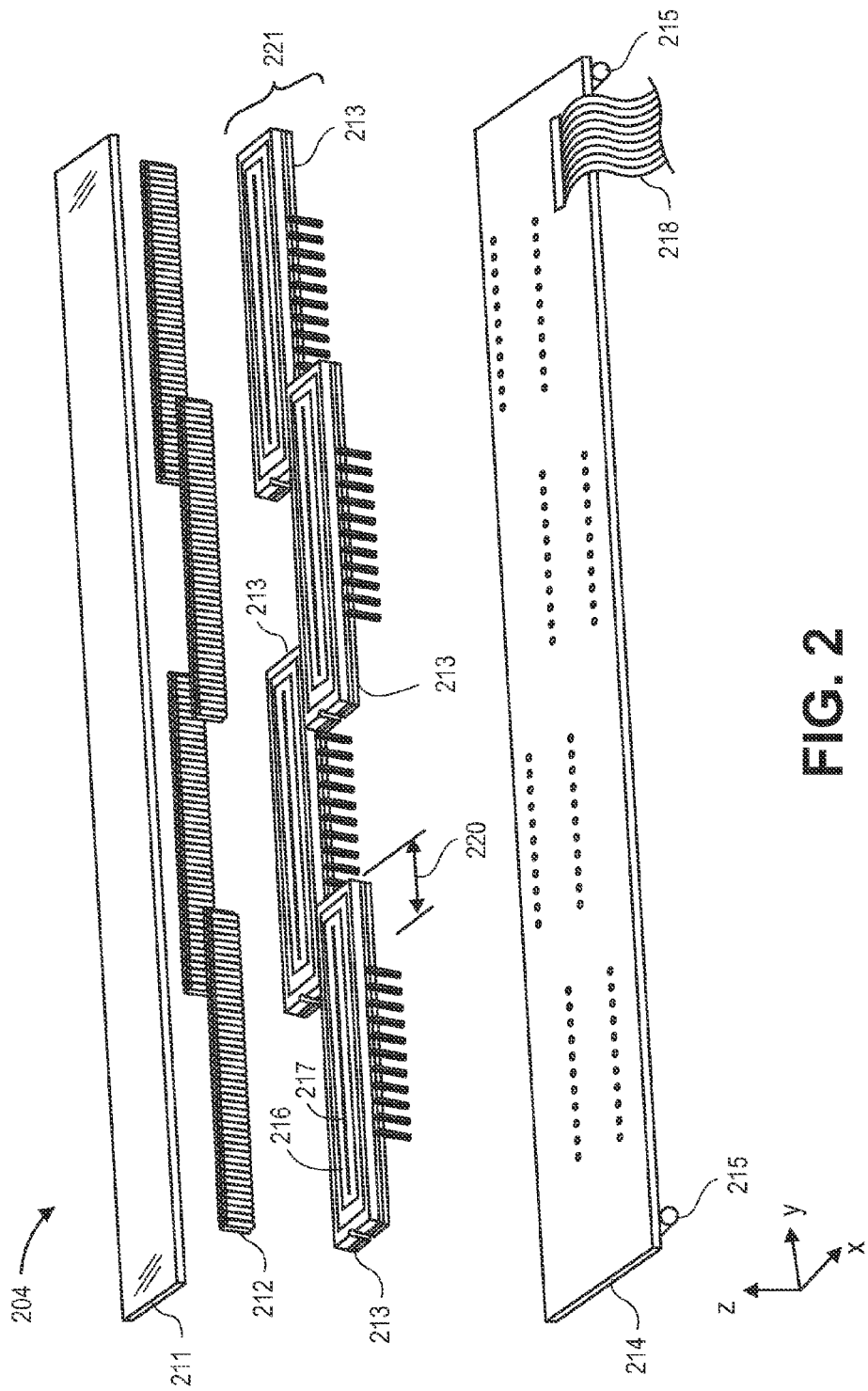
FIG. 2 is an exploded illustration of a detector bar in accordance with an embodiment.

FIG. 2 illustrates a detector bar in accordance with an embodiment. Detector bar 204 includes GRIN lenses 212, shown without conformal blocks that customarily surround them, and linear CCD image sensors 213, packaged as integrated circuit (IC) chips. During assembly of a scanner, linear CCD image sensors 213 are soldered into printed circuit board (PCB) 214 and electrically connected with other circuits through ribbon cable 218. The ICs house CCD pixel elements 217 protected by glass window 216. The CCD pixel elements include CCD photodiodes, a conductor matrix connected with a CCD transfer array, and other elements as found in CCDs.

Guides 215 allow detector bar 204 to travel back and forth in a lateral, x direction in order to scan a sample. Protective window 211 shields GRIN lenses 212 from wet membranes and fixes the sample at a working, focal distance of the GRIN lenses.

Detector bar 204 includes multiple CCD image sensor ICs 213. Multiple CCD image sensors 213 are staggered in both directions so as to effectuate a longer, contiguous line of imaging that covers the desired total scan width. For example, four linear CCD chips that each image a 28.67 mm-long line can be staggered 27.5 mm along their lengths and 10 mm along the perpendicular direction to allow for scanning 4×27.5=110 mm wide. The packaging of each IC chip is invariably larger than its CCD photodiode sensing array. The 10 mm offset in the lateral direction allows for placing the line imagers so that their sensor arrays have some overlap along the longitudinal direction.

Linear CCD image sensor ICs 213 are arranged in staggered fashion 221 with respect to each other longitudinally along the detector bar. They overlap each other longitudinally (in the y direction) by distance 220 so that an end of the line of pixels 217 from one chip are aligned with or slightly overlap the beginning of the line of pixels 217 from the next chip. For a Toshiba TCD1205DG linear CCD chip as currently specified, distance 220 should be at least 6.46±0.8 mm.

Figure 3:
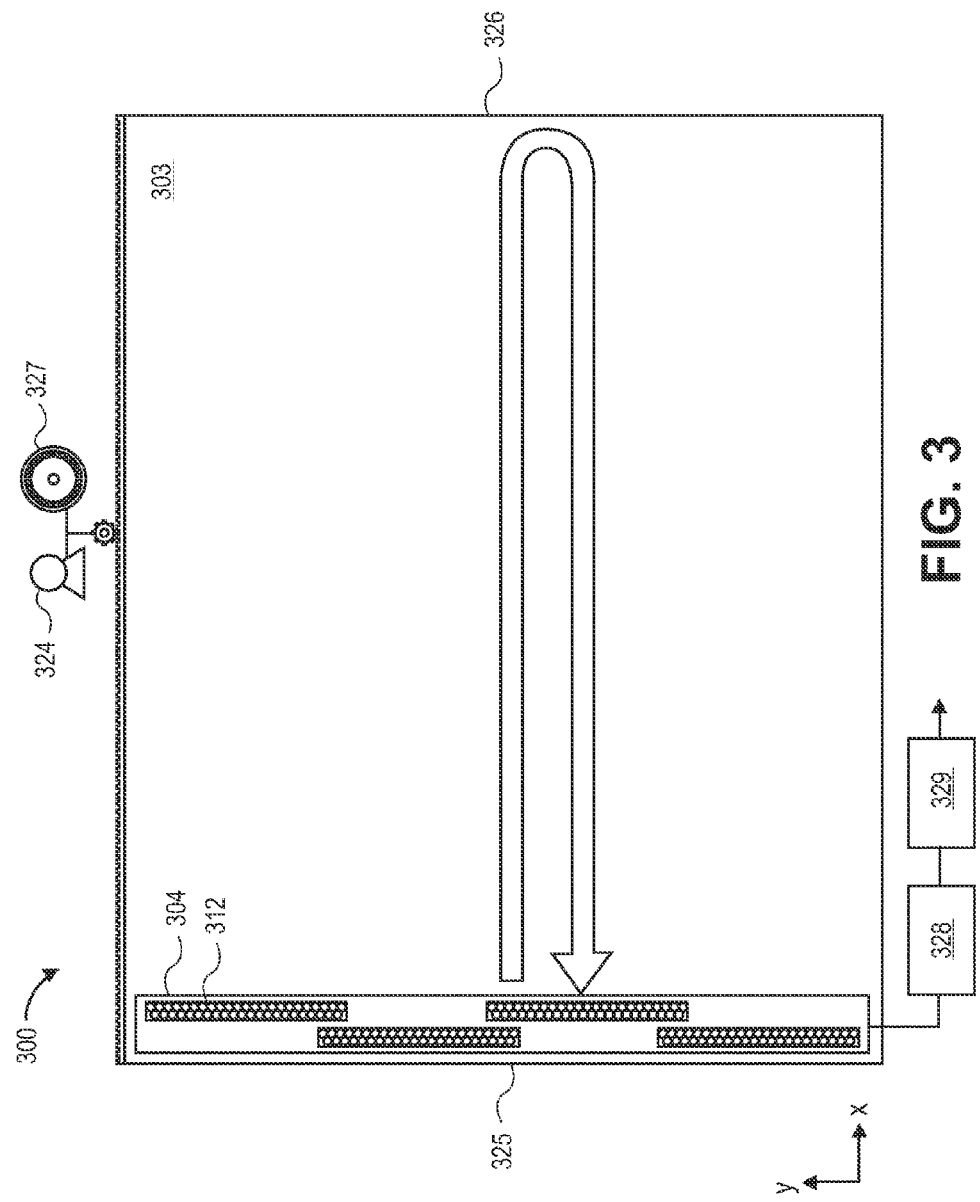
FIG. 3 illustrates a top view of a sample bed with a single detector bar in accordance with an embodiment.

FIG. 3 illustrates a top view of a sample bed with a single detector bar in accordance with an embodiment. Single detector bar scan system 300 includes sample bed 303, detector bar 304 (with the tops of GRIN lenses 312 shown in the figure), and stepper motor 324 coupled with detector bar 304 to move it accurately and precisely along the x direction. Optional optical encoder 327 can be used to determine a precise position of the detector bar at any point.

For a scan, detector bar 304 starts from end 325, moves while detecting pixels to opposite end 326, and then moves while detecting pixels back to end 325. Movement (and any stops between) from end 325 to end 326 can be referred to as a "first pass," and movement (and any stops between) from end 326 back to end 325 can be referred to as a "second pass." A combination of a first and second pass can be referred to as a "contra-directional scan."

Detecting of pixels during a pass can occur while the detector bar is actually in motion or at miniature, stepped stops between subsequent motions during the pass.

At each particular (x, y) position during the first pass, an amount of light $a_{x,y}$ is detected and stored. The total image from all the (x, y) positions from the first pass can be stored as matrix A (e.g., a two-dimensional array). At each particular (x, y) position during the second pass, an amount of light $b_{x,y}$ is detected and stored. The total image from all the (x, y) positions from the second pass can be stored as matrix B. A final image can be prepared by averaging each point of the A matrix with each point of the B matrix, i.e., C=(A+B)/2 in matrix notation. Averaging can be done after both images are fully taken or in small steps as each second measurement is taken.

"Combining" each point from different passes can be accomplished through averaging, summing (i.e., without division by the number of passes), or otherwise subjecting to a function that depends on the readings from the point from the multiple passes. Mathematically, an intensity I at each location (x, y) on passes 1 through N can be combined in a generic functional relationship: $I_{x,y}^{combined} = f(I_{x,y}^{pass\ 1}, \ldots, I_{x,y}^{pass\ N})$.

Combining can be accomplished in circuit 328. The circuit may be a dedicated hardware or firmware circuit, or it can be a more general purpose memory and processor for use with other functions of the device. Circuit 328 is programmed or otherwise adapted to combine a pixel reading from a position in the first pass with a pixel reading from the position in the second pass. Circuit 329, which can also be a general processing circuit running software or a more specialized circuit, is programmed to construct a two-dimensional image from the combined pixel readings. The output image can be in a format that can be read by a personal computer or other computing device.

Multiple contra-directional scans can be performed in order to further refine the image. That is, 4, 6, 8, or more passes can be used and their (x, y) pixels averaged or otherwise combined. Images from later contra-directional scans can be weighted differently than images from previous contra-directional scans to statistically compensate for less photons being collected later from samples that dim over time. An odd number of passes, that is, 3, 5, 7, or more passes, can be used as well. For example in a 3-pass system, the $1^{st}$ and $3^{rd}$ passes can be averaged together, and then the average combined with the $2^{nd}$ pass.

Figure 4:
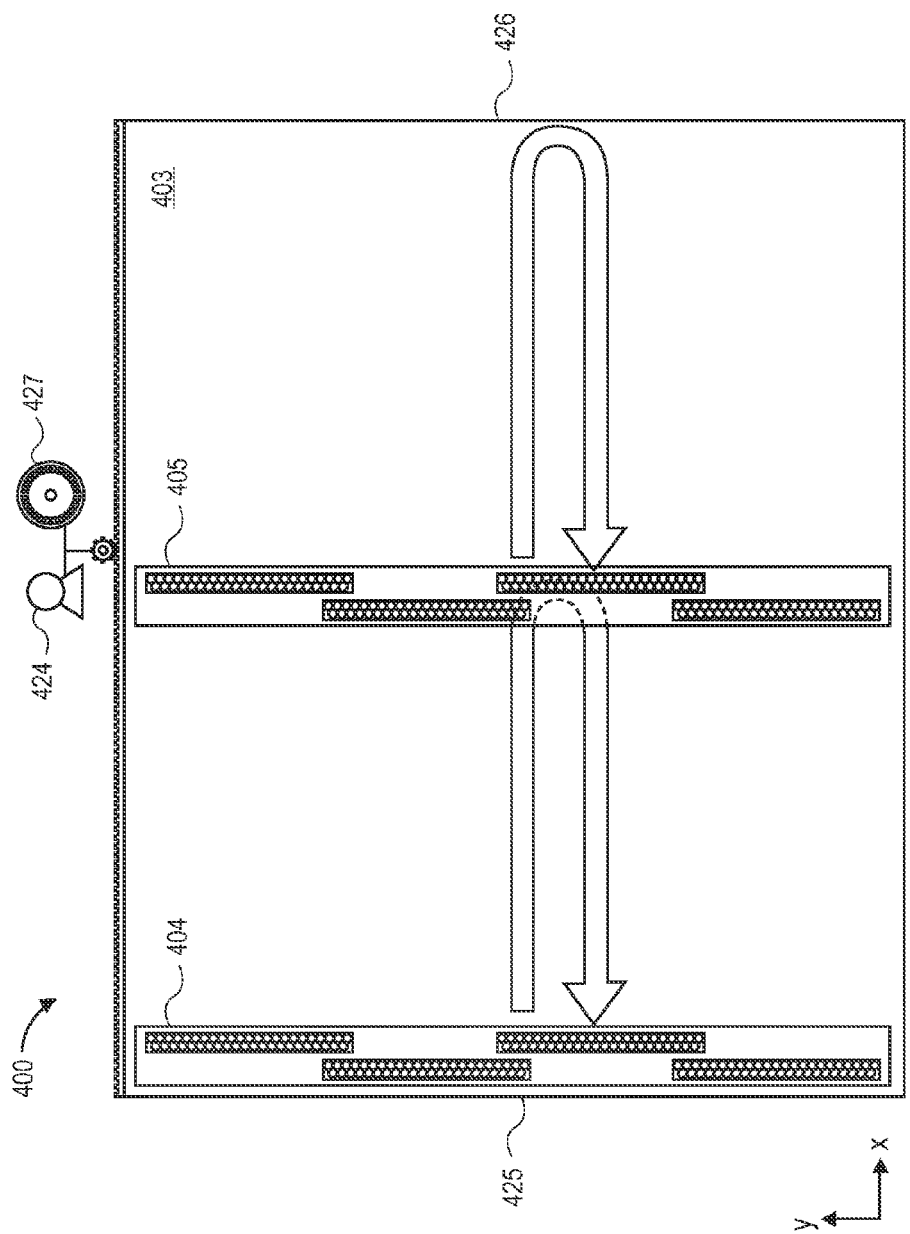
FIG. 4 illustrates a top view of a sample bed with multiple detector bars in accordance with an embodiment.

FIG. 4 illustrates a top view of a sample bed with multiple detector bars in accordance with an embodiment.

Dual detector bar scan system 400 includes sample bed 403, detector bars 404 and 405, and stepper motor 424 coupled with line imagers 404 and 405 to move them accurately and precisely along the x direction. Optical encoder 427, which can be encased in the motor, can be used to determine precise positions of the line imagers at any point.

For a first pass, line imager 404 starts from end 425, moves while detecting pixels a little past the middle of sample bed 403, and then moves while detecting pixels back to end 425. Similarly, line imager 405 starts from a little before the middle of sample bed 403, moves while detecting pixels to end 426, and then moves while detecting pixels back to the middle position from whence it came.

Both line imagers can be mechanically scanned together along the x-axis. To cover a scan length of 10 cm, the scanner can have the line imagers spaced 5 cm apart and both scanned 5 cm+10 mm along the x-direction. The extra 10 mm can be to account for the x-offset in the positioning of the line imagers. In this way, both scan heads cover a common 5 cm length.

For a given exposure time per line read, the use of two scan heads instead of one allows for scanning half the distance and therefore covers the same area twice as fast as would be achievable with a single scan head. Multiple scan bars for speed is not required for document or book scanning or other externally illuminated scanning because one can control and keep steady the amount of light that illuminates the target. For chemiluminescence and other dim luminescence that changes over time, multiple scan bars can reduce errors resulting from non-linear dimming.

Faster imaging can be obtained by adding even more scan heads along the x-axis. For example, 3, 4, 5, or more line imagers can scan a sample. CCDs on the imagers can be calibrated with one another before or after a scan. Adding more CCDs along the y-axis allows for scanning a wider scan area.

An alternative way to effectuate the scan is to move the sample instead of the scan heads with respect to the inertial frame (i.e., the ground). That is, a motor can move the sample medium back and forth while the detector bar remains still. In other embodiments, both the sample and the scan head can be moved opposite one another.

Figure 5:
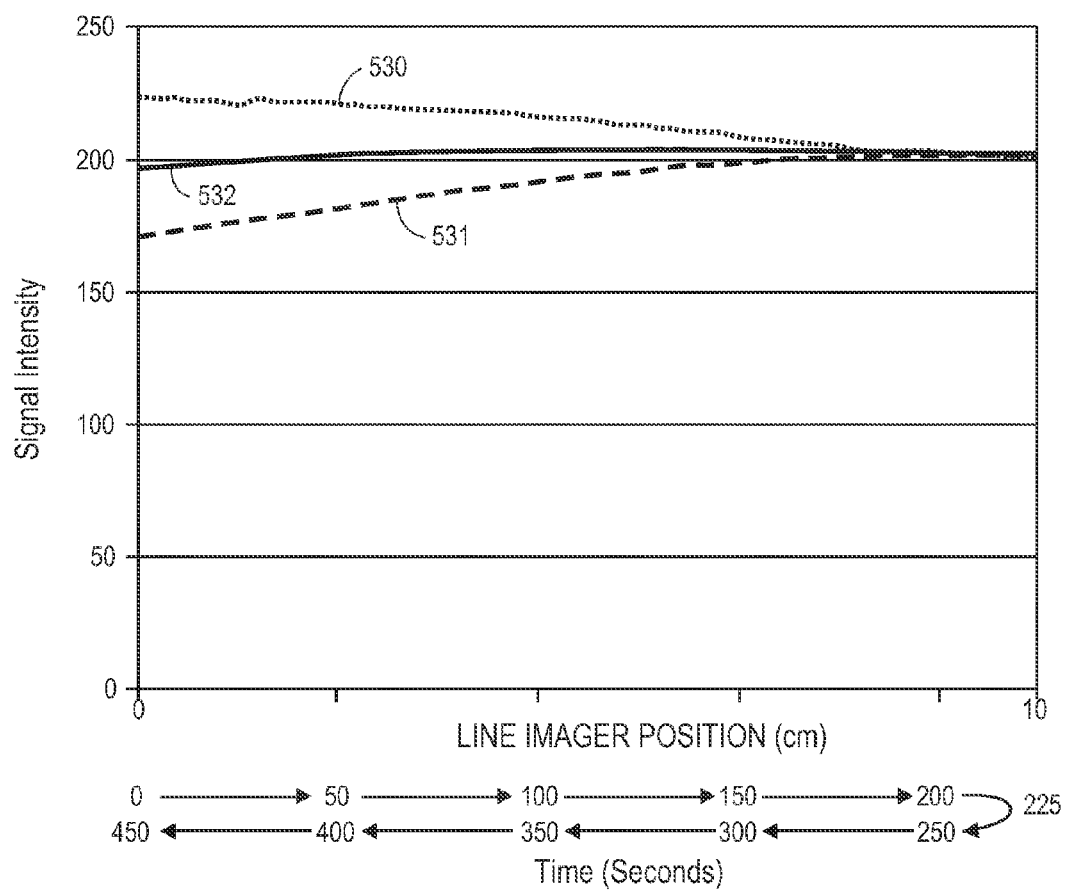
FIG. 5 is a chemiluminescence plot with respect to time on multiple sweeps.

FIG. 5 is a chemiluminescence plot with respect to time on two sweeps. On first mechanical pass 530 of the scanner from position 0 to position 10 (from 0 to 225 seconds), the signal decreases over time. On second mechanical pass 531 of the scanner from position 10 back to position 0 (from 225 to 450 seconds), the signal decreases more over time. Averaging the two passes together at each point in time—or more accurately, at each x location—produces a relatively flat, horizontal average signal 532, which is more constant than the individual signals.

A scan time on the order of a few minutes per pass is relatively short compared to time course changes of many CL substrates used in the Western Blot chemiluminescence market today. Chemiluminescence ramps up quickly upon initiation (e.g., after probing with a second biomolecule), ramping up to its maximum luminescence within about 10 minutes. Luminescence intensity begins to fall off linearly for the next hour and continues to fade after that.

It has been found that a 2, 3, 4, or 5 minute scan time is sufficiently short compared to the rate of change of chemiluminescence intensity. Even though there is some change within such a window, the change is relatively linear. Averaging or summing two contra-directional scans together can remove most of that change, and the result is predominantly constant over the scan position as shown in the figure. Thus, quantification based on actual concentration of the sample and not imager variation can be enabled.

An estimate of the residual error after contra-directional averaging can be calculated. Assuming a constant emitted optical power $P_0$ from position 0 to position L along a scan direction x and a slow varying change during each pass, the power levels for the first pass $P_1(x)$ and second pass $P_2(x)$ can be represented by the functions:

$$P_1(x) = P_0\left(1 + a\left(\frac{x}{L}\right)^b\right) \qquad \text{(Eqn. 1)}$$

$$P_2(x) = P_0\left(1 + a\left(\frac{2L-x}{L}\right)^b\right) \qquad \text{(Eqn. 2)}$$

where a and b are constants based on the type of CL substrate involved and L is the total x-direction length. The difference (error $\epsilon$) between the power levels and the average can be derived as:

$$\varepsilon \equiv \frac{[P_1(L) + P_2(L)] - [P_1(0) + P_2(0)]}{2P_o} = a(1 - 2^{b-1}) \qquad \text{(Eqn. 3)}$$

Given values of a=0.05 and b=0.5 (i.e., a square root dependence), contra-directional averaging reduces the error from 5% with no correction to less that 1.5%. The shorter the scan time, the more linear the change, and the more accurate the correction.

Figure 6:
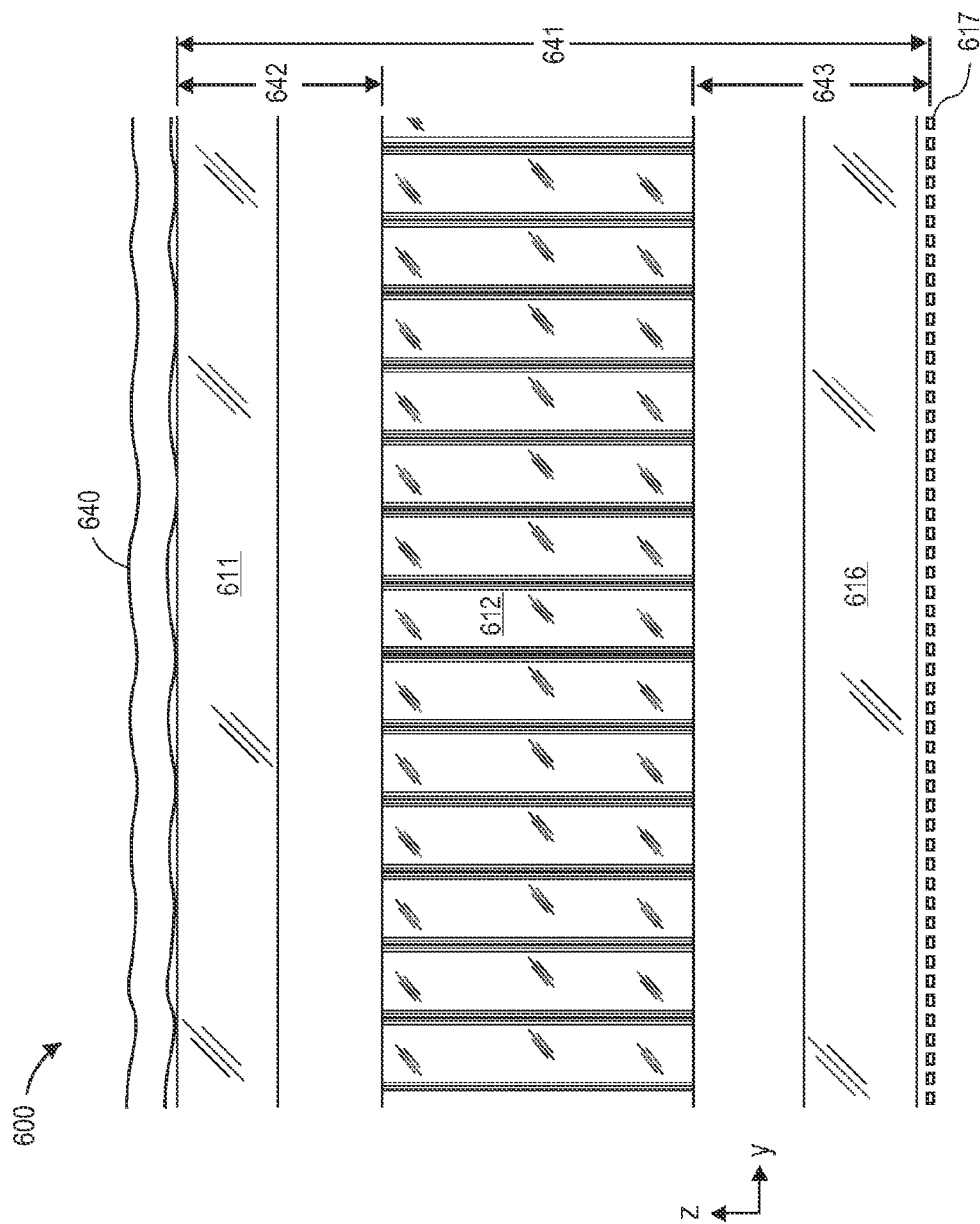
FIG. 6 illustrates an elevation, cross-section view of high NA optics placement in accordance with an embodiment.

FIG. 6 illustrates an elevation cross-section view of high NA optics placement in accordance with an embodiment. Sample 640, such as a CL Western blot membrane, is placed on top of scan window 611. Emitted light emanating from various points is collected by a GRIN lens array 612 and projected onto a linear CCD pixel elements 617. The latter is sealed with a glass window 616. A light-tight enclosure surrounds system 600 to prevent ambient light from entering inside of the scanner and fouling measurements.

The top surface of scan window 611 upon which membrane 640 rests is positioned at distance 642 from GRIN lenses 612 to be at their front working distance. On the other side of the lenses, the CCD pixel elements are positioned at distance 643 from GRIN lenses 612 to be at their back working distance. It has been found that total working distance 641 can be much smaller than whole-sample imagers, which use low-NA lenses.

Wide pixel sizes (e.g., 200 μm) can help with collecting more light efficiently. To further increase light collection and obtain equal resolution in both directions, pixel charges can be binned together.

Figure 7:
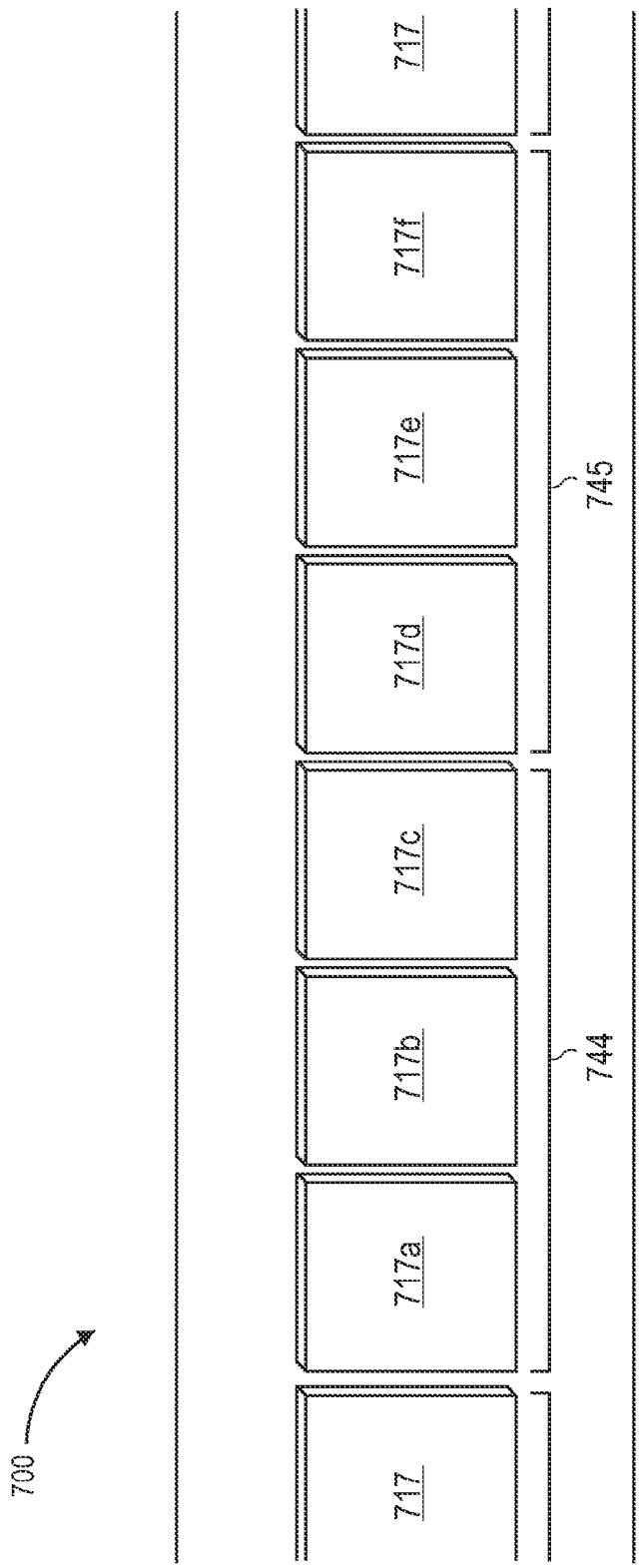
FIG. 7 illustrates a top view of simplified linear CCD array pixels in accordance with an embodiment.

FIG. 7 is a top down view of CCD pixels in accordance with an embodiment. Photo-charges collected by multiple adjacent CCD pixels 717a through 717c are binned together in bin 744, and photo-charges collected by pixels 717d through 717f are binned together in bin 745.

For the Toshiba TCD1205DG (discussed above) having 14 μm long and 200 μm wide pixels, binning 14 pixels in a row, that is, binning by 14, results in an effective pixel size of 14×14 μm=196 μm, which is close to the 200 μm width size of the pixels. The 196 μm×200 μm effective pixel size is almost square. Other binning levels can be applied and scan step sizes changed to produce higher or lower resolution scans. For example, binning by 7 and a scan step of 98 μm results in scanning resolution of 98 μm in both directions.

Doubling the effective pixel size quadruples the amount of collected light and reduces resolution by half. For CL Western Blots, where the bands are multiple millimeters in size, an embodiment with a resolution of 200 μm produces reasonably good quality images.

With an embodiment, comparable LOD is achievable with exposures that are orders of magnitude shorter than what is needed for wide-area imaging. For example, a 0.5 second exposure time per line read gives a similar LOD to what a commercial wide-area CCD imager can give in a 2 minute exposure time. This short, 0.5 second exposure allows reading multiple lines, through linear scanning, to obtain an image of the same area size in a comparable total imaging time.

On-Chip Binning

A typical linear CCD has an array of imaging diodes arranged in a straight line. When light falls on these diodes, each diode creates a photo-charge that is proportional to the amount of light that lands on that photodiode. After an amount of time, referred to as the exposure time, a signal, often called diode transfer, is used to transfer the photo-charges in the photodiodes into a CCD transfer array. The CCD transfer array moves the individual photo-charges towards one end of the CCD transfer array. The CCD transfer array moves the photo-charges in steps. The CCD transfer array is usually controlled by at least one clock signal and in many cases more than one clock signal. The number of clocks required is determined by the design of the CCD involved. Typically the CCD transfer array will move the photo-charges one step for each clock edge of the clock signals that drive the CCD transfer array.

At the end of the CCD transfer array is a readout capacitor. As the CCD shifts photo-charges along the CCD transfer array, they eventually reach and move into this readout capacitor. As part of the readout process of the CCD, this capacitor is periodically pre-charged. Usually this capacitor is pre-charged immediately before the CCD transfer array shifts in a photo-charge from one photodiode. If the readout capacitor is pre-charged immediately before a photo-charge is moved into it, the change in voltage of the readout capacitor is proportional to the amount of photo-charge injected into it by the CCD transfer array. The voltage of the readout capacitor is typically buffered by an amplifier on the CCD IC and presented on an output pin. The voltage at the output pin is typically further amplified, low pass filtered, and digitized by other electronics in an imaging system. Normally, pixels are read out of the linear CCD one at a time. Therefore, electronics normally read out the photodiode charges in alternating fashion, alternating between precharging the readout capacitor, measuring and storing the pre-charge voltage, clocking the CCD transfer array to move one photodiode charge into the readout capacitor, and then reading the voltage present at the output pin of the linear CCD array IC. At that point the photodiode charge can be computed. The photo-charge is proportional to the change in voltage of the readout capacitor between its pre-charge voltage and voltage with photo-charge injected.

Unfortunately the process of measuring the voltage of the readout capacitor is a noisy process. There are various forms of electrical noise that add themselves into the voltage that is measured. This noise can obscure the desired signal that is being read from the readout capacitor. These noise sources that corrupt the voltage read from the readout capacitor are often referred to as "readout noise."

A way to increase the signal-to-noise ratio in the presence of readout noise is to perform a readout sequence that is referred to as "on-chip binning." In on-chip binning, the readout sequence of the CCD array is modified. In this modified sequence the readout capacitor is pre-charged and then the CCD array is clocked so that the photo-charges from multiple adjacent photodiodes are moved into the readout capacitor. The change in voltage of the readout capacitor, and hence the output pin, is proportional to the total photo-charge moved into the readout capacitor from multiple photodiodes. The spatial resolution of the linear imaging system is reduced because photodiode charges from multiple pixels are lumped together, but the signal to noise ratio is typically improved because the readout noise remains relatively constant while the change in voltage typically increases.

On-chip binning can be accomplished by controlling the readout pins of a CCD. The readout pins of a Toshiba TCD1205DG that should be controlled for on-chip binning include Reset (RS), Boost (BT), Phase 1 (Ø1), and Phase 2 (Ø02). This can be done without a significant increase in 1/f noise (i.e., flicker noise).

Variable CCD Clocking

An aspect of some embodiments is to vary the speed of the linear CCD readout clocks. This can improve the signal to noise ratio of the image. As mentioned earlier there are several sources of noise that corrupt the voltage presented by the output amplifier of the linear CCD array. Two of the noise sources are flicker noise, often called 1/f noise, and white noise.

Many imaging CCD arrays implement a method for reducing flicker noise. The method is to apply a fixed preset voltage to the readout capacitor of the CCD array. The imaging system will sample and store the value of the preset voltage driven out of the output pin of the imaging CCD array. After the preset voltage is measured, the imaging system will manipulate the CCD signals to move some number of photo-charges in the CCD array into the readout capacitor. After the photo-charges have been moved into the readout capacitor, the imaging system will sample the voltage presented at the output of the CCD IC. The measured and stored preset voltage is subtracted from the photo-charge voltage. This subtraction tends to remove the flicker noise.

In order to provide the maximum reduction in flicker noise, it is advantageous to sample the preset voltage and the photo-charge voltage as quickly together in time as possible. If on-chip binning is used, then the binning should occur as quickly as possible in order to cause the preset voltage and photo-charge voltages to be sampled closely together in time. In order to achieve the maximum binning speed, the signals that cause the photo-charges in the CCD array to move into the readout capacitor should be operated at a high rate. In many cases the high rate is the maximum recommended rate in the data sheet for the imaging CCD array. Another benefit of the fast binning is the overall reduction in readout time and therefore the total time for producing an image.

A second source of readout noise is white noise. White noise has a uniform noise power over a wide range of frequencies. One method of reducing readout noise is to electronically low pass filter the output signal of the CCD array. By properly limiting the bandwidth of the signal before it is sampled, much of the white noise can be rejected while allowing most of the signal to be measured. This helps increase the signal to noise ratio. Low pass filtering reduces the slew rate of the readout signal presented to the imaging system from the CCD IC.

In order to accurately measure the preset voltage presented by the CCD, the CCD should be operated to cause it to present its preset voltage at the output of the CCD, then the preset voltage must be allowed to propagate though the low pass filter. After some amount of time the preset voltage will have settled to very close to its final value. At this point in time, the imaging system will sample the preset voltage and store it to remove flicker noise later. While the imaging system is waiting for the preset voltage level to settle at the output of the white noise-removing low pass filter, it should cease clocking the photo-charges through the CCD array. After sampling the preset voltage, the imaging system will clock the photo-charges into the readout capacitor at a high rate to accomplish on-chip binning. After the pixels have been binned, the imaging system will stop operating the clock signals for the CCD array. The photo-charge voltage at the output of the CCD array will be allowed to propagate through the white noise-removing low pass filter until the voltage settles to within some desired percentage of its final value. At this point the imaging system will sample the photo-charge voltage.

A method of binning implemented in some embodiments results in at least three clocking rates of the CCD array. There is one rate in which the CCD clock signals are not operated while the preset voltage settles and is then measured. There is a second rate in which the CCD clock signals are operated at a high rate to achieve rapid on-chip binning And there is a third rate in which the CCD clocks are paused while the photo-charge voltage of the binned photo-charges settles and is then measured. Multiple clock-out rates in conjunction with pixel on-chip binning can maximize the signal to noise ratio of the resulting image.

Figure 8:
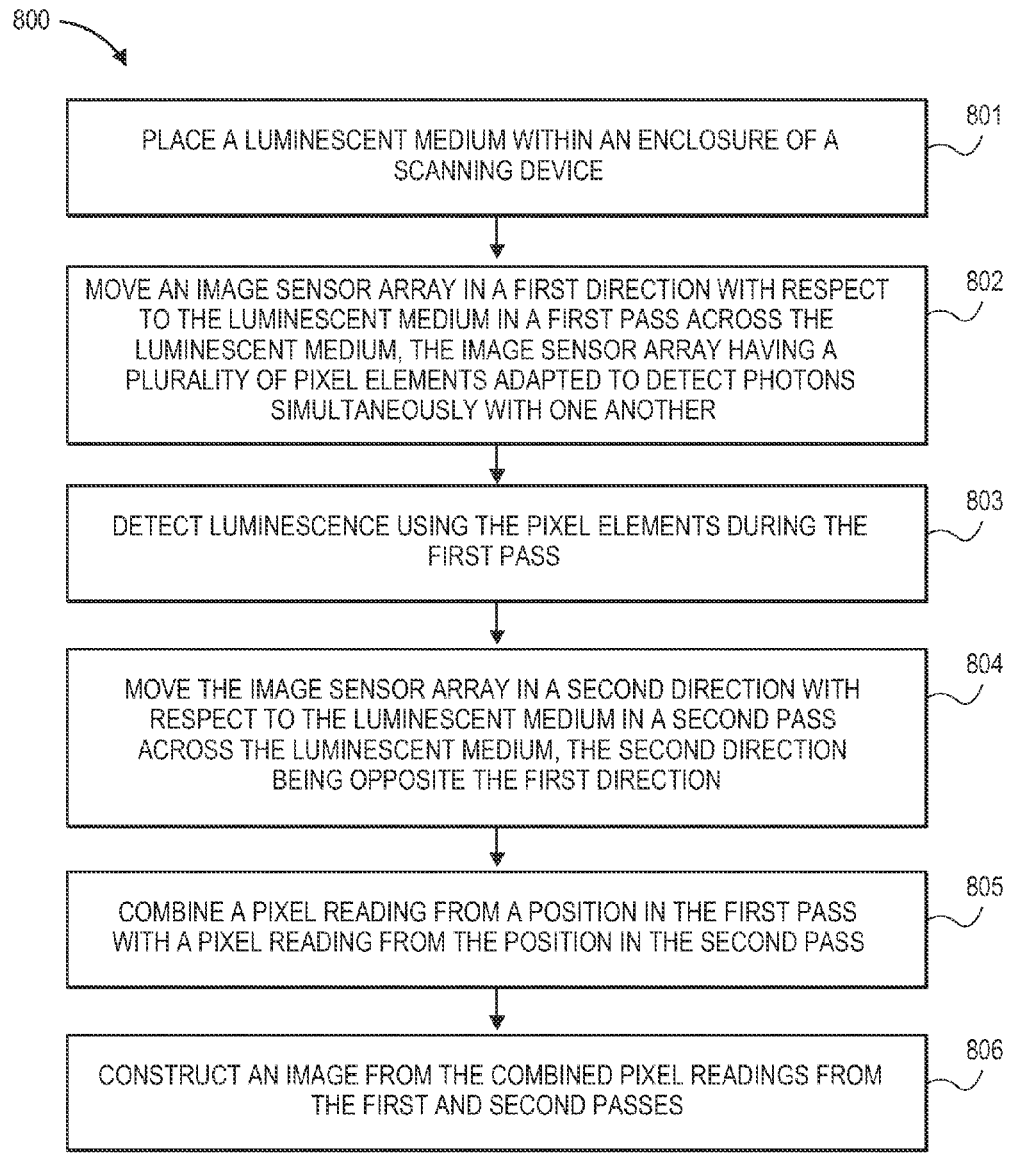
FIG. 8 is a flowchart of a process in accordance with an embodiment.

FIG. 8 is a flowchart of a process in accordance with an embodiment. In operation 801, a luminescent medium is placed within an enclosure of a scanning device. In operation 802, an image sensor array is moved in a first direction with respect to the luminescent medium in a first pass across the luminescent medium, the image sensor array having a plurality of pixel elements adapted to detect photons simultaneously with one another. In operation 803, luminescence is detected using the pixel elements during the first pass. In operation 804, the image sensor array is moved in a second direction with respect to the luminescent medium in a second pass across the luminescent medium, the second direction being opposite the first direction. In operation 805, a pixel reading from a position in the first pass is combined with a pixel reading from the position in the second pass. In operation 806, an image is constructed from the combined pixel readings from the first and second passes.

FIG. 9 is a flowchart of a process in accordance with an embodiment. In operation 901, target biomolecules are fixed to a sample medium in a spatial pattern, the pattern including information about an identity of the target biomolecules. In operation 902, the target biomolecules are probed with a primary probe biomolecule that has a binding affinity for the target molecule. In operation 903, the primary probe molecule is probed with a secondary probe biomolecule that has a binding affinity for the primary probe biomolecule, the secondary probe biomolecule having enzymatic activity that triggers the generation of detectable energy through a change in a substrate biomolecule, wherein the substrate biomolecule is a substrate for the enzymatic activity of the secondary probe biomolecule. In operation 904, one scans across the sample medium in at least one spatial dimension with a charge-coupled device (CCD) detector, the CCD detector scanning across the sample medium at a fixed distance of between 1 millimeter and 100 millimeters from the sample medium. In operation 905, an image sensor array is moved across the sample medium in at least on spatial dimension in a first pass. In operation 906, luminescence is read by the image sensor array during the first pass. In operation 907, the image sensor array is moved across the sample medium in the at least one spatial dimension in a second pass. In operation 908, luminescence is read by the image sensor array during the second pass. In operation 909, luminescence readings taken at a position from the first and second passes are combined. In operation 910, an image is constructed from the combined readings taken at the position from the first and second passes. In operation 911, the identity of the target biomolecules is determined by correlating the detected detectable energy to the spatial pattern.

While the invention has been described by way of example and in terms of the specific embodiments, it is to be understood that the invention is not limited to the disclosed embodiments. To the contrary, it is intended to cover various modifications and similar arrangements as would be apparent to those skilled in the art. Therefore, the scope of the appended claims should be accorded the broadest interpretation so as to encompass all such modifications and similar arrangements.

What is claimed is:

1. A luminescence scanner apparatus comprising:
    a sample bed configured to hold a luminescent sample medium;
    a detector bar comprising one or more image sensor arrays, each image sensor array having a plurality of pixel elements, the pixel elements adapted to detect photons simultaneously with one another, the detector bar configured to move with respect to the sample bed, the at least one of the one or more image sensor arrays comprising a charge-coupled device (CCD) sensor array integrated within an integrated circuit (IC);
    a motor configured to move the detector bar with respect to the sample bed in a first direction and move the detector bar with respect to the sample bed in a second direction opposite the first direction;
    a circuit operatively coupled with the motor and having instructions to move the detector bar with respect to the sample bed in the first direction in a first pass and store a first pixel reading from a position in the first pass and then to move the detector bar with respect to the sample bed in the second direction in a second pass and take a second pixel reading at the same position during the second pass and combine the pixel readings of the same position from the first and second passes;
    a circuit having instructions to construct an image from the combined pixel reading; and
    a circuit having instructions to:
        apply a first CCD clock frequency to the CCD sensor array; and then
        apply a fixed preset voltage to a readout capacitor of the CCD sensor array;
        sample a value of the preset voltage on one or more output pins on the CCD sensor array; and then apply a second CCD clock frequency to the CCD sensor array; and then
clock multiple photon-induced charges from adjacent CCD pixel elements into the readout capacitor of the CCD sensor array.

2. The apparatus of claim 1 wherein combining the pixel readings includes averaging the pixel reading from the position in the first pass with the pixel reading from the same position in the second pass.

3. The apparatus of claim 1 wherein the CCD sensor array is integrated within an integrated circuit (IC), the apparatus further comprising:
a circuit having instructions to sum multiple photo-charges from adjacent CCD photodiodes into a readout capacitor of the CCD sensor array,
thereby increasing a signal to noise ratio of the CCD sensor array.

4. The apparatus of claim 1 wherein the one or more image sensor arrays are not cooled below 0 degrees Celsius.

5. The apparatus of claim 1 wherein the detector bar comprises a plurality of linear image sensor array integrated circuits (ICs) staggered with respect to each other along the detector bar.

6. The apparatus of claim 5 wherein the linear image sensor array ICs overlap one another longitudinally on the detector bar.

7. The apparatus of claim 1 further comprising:
a second detector bar comprising one or more image sensor arrays, the second detector bar configured to move with respect to the sample bed,
wherein the detector bars are configured to scan over different, non-overlapping areas of the sample bed; and
a circuit having instructions to construct the image from pixel readings from both of the detector bars.

8. The apparatus of claim 7 wherein the detector bars are further configured to scan over a common, overlapping portion of the sample bed in addition to their respective non-overlapping areas.

9. The apparatus of claim 1 wherein the detector bar is configured to be moved and the sample bed is configured to be physically stationary.

10. The apparatus of claim 1 wherein the luminescent sample medium is selected from a nylon membrane, a nitrocellulose membrane, and a well plate.

11. The apparatus of claim 1 further comprising:
a gradient index (GRIN) lens array disposed between the sample bed and the one or more image sensor arrays, the GRIN lens array having a working numerical aperture (NA) of greater-than-or-equal-to 0.10.

12. The apparatus of claim 11 wherein the GRIN lens array is disposed between 1 and 100 millimeters of the sample bed.

13. The apparatus of claim 1 further comprising:
a light tight enclosure configured to enclose the sample bed.

14. The apparatus of claim 1 wherein the first pass occurs over an amount of time and the second pass occurs over an equal amount of time.

15. A luminescence scanner apparatus comprising:
a sample bed configured to hold a luminescent sample medium;
a moveable detector bar comprising one or more image sensor arrays comprising a charge-coupled device (CCD) sensor array integrated within an integrated circuit (IC);
a circuit having instructions to:
move the detector bar in a first pass and take a first pixel reading at a position in the first pass;
move the detector bar in an opposite direction in a second pass and take a second pixel reading at the same position during the second pass; and
combine the pixel readings of the same position from the first and second passes;
a circuit having instructions to construct an image from the combined pixel reading; and
a circuit having instructions to:
apply a first CCD clock frequency to the CCD sensor array; and then
apply a fixed preset voltage to a readout capacitor of the CCD sensor array;
sample a value of the preset voltage on one or more output pins on the CCD sensor array; and then
apply a second CCD clock frequency to the CCD sensor array; and then
clock multiple photon-induced charges from adjacent CCD pixel elements into the readout capacitor of the CCD sensor array.

16. The apparatus of claim 15 wherein combining the pixel readings includes averaging the pixel reading from the position in the first pass with the pixel reading from the same position in the second pass.

17. The apparatus of claim 15 wherein at least one of the one or more image sensor arrays comprises a charge-coupled device (CCD) sensor array.

18. A luminescence scanner apparatus comprising:
a sample bed with a light tight enclosure, the sample bed configured to hold a luminescent sample medium;
a moveable detector bar comprising one or more uncooled charge-coupled device (CCD) image sensor arrays;
a circuit having instructions to:
move the detector bar in a first pass and take about 0.5 second exposure pixel readings during first pass;
move the detector bar in an opposite direction in a second pass and take about 0.5 second exposure pixel readings during the second pass; and
combine the pixel readings from the first and second passes;
a circuit having instructions to construct an image from the combined pixel readings; and
a circuit having instructions to:
apply a first CCD clock frequency to the CCD sensor array; and then
apply a fixed preset voltage to a readout capacitor of the CCD sensor array;
sample a value of the preset voltage on one or more output pins on the CCD sensor array; and then
apply a second CCD clock frequency to the CCD sensor array; and then
clock multiple photon-induced charges from adjacent CCD pixel elements into the readout capacitor of the CCD sensor array.

19. The apparatus of claim 18 wherein one of the circuits has instructions to combine pixel readings from three or more passes of the detector bar.

* * * * *